United States Patent [19]

Yost

[11] Patent Number: 4,823,609
[45] Date of Patent: Apr. 25, 1989

[54] ULTRASONIC METHOD AND APPARATUS FOR DETERMINING CRACK OPENING LOAD

[75] Inventor: William T. Yost, Newport News, Va.

[73] Assignee: The United States of America as represented by the Administrator of the National Aeronautics and Space Administration, Washington, D.C.

[21] Appl. No.: 210,277

[22] Filed: Jun. 23, 1988

[51] Int. Cl.⁴ .............................................. G01N 19/08
[52] U.S. Cl. ...................................................... 73/799
[58] Field of Search ........................... 73/799, 577, 598

[56] References Cited

U.S. PATENT DOCUMENTS

| | | |
|---|---|---|
| 3,911,734 | 10/1975 | Mehdizadeh . |
| 4,265,120 | 5/1981 | Morris et al. ........................ 73/600 |
| 4,522,064 | 6/1985 | McMillan ............................ 73/592 |
| 4,534,219 | 8/1985 | Nadeau et al. ...................... 73/587 |
| 4,669,311 | 6/1987 | McKinnon .......................... 73/598 |
| 4,689,996 | 9/1987 | Huschelrath ........................ 73/643 |
| 4,763,528 | 8/1988 | Bouami et al. ...................... 73/799 |

Primary Examiner—Jerry W. Myracle
Attorney, Agent, or Firm—Harold W. Adams; John R. Manning; Charles E. B. Glenn

[57] ABSTRACT

An ultrasonic apparatus determines crack opening load by placing a transmit transducer on one side of the crack and a receive transducer on the opposite side of the crack. An acoustic signal passing through a region of the crack is mechanically rectified to produce a second harmonic of an input signal. A harmonic output signal of the receive transducer is converted into an electrical signal and the peak harmonic amplitude is determined while increasing a tension load on the specimen. The peak harmonic amplitude indicates crack opening load.

12 Claims, 3 Drawing Sheets

FIG. 7
FIG. 9
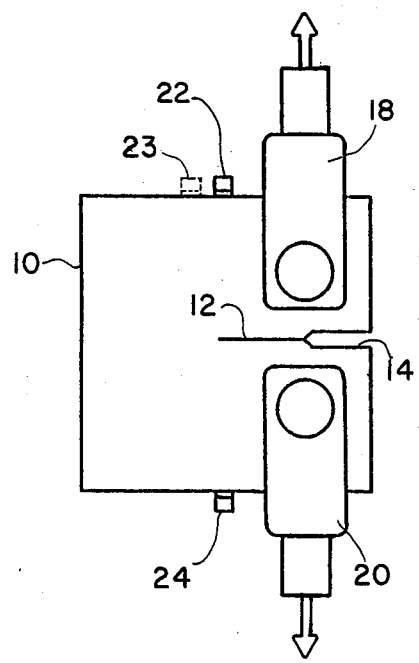
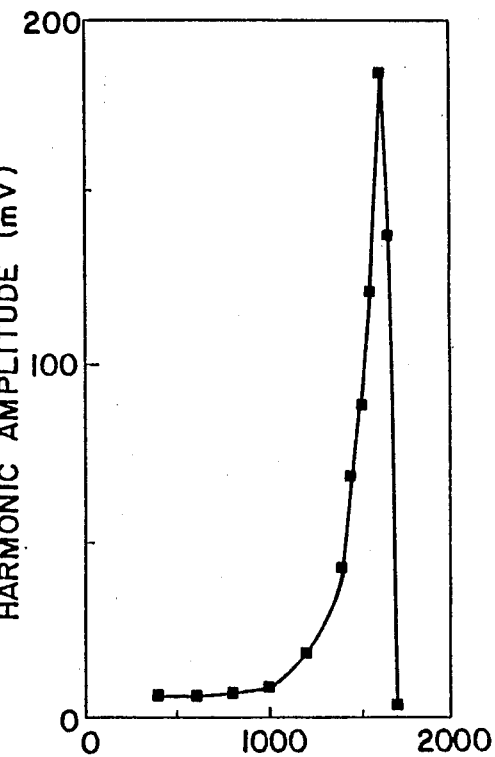
FIG. 8
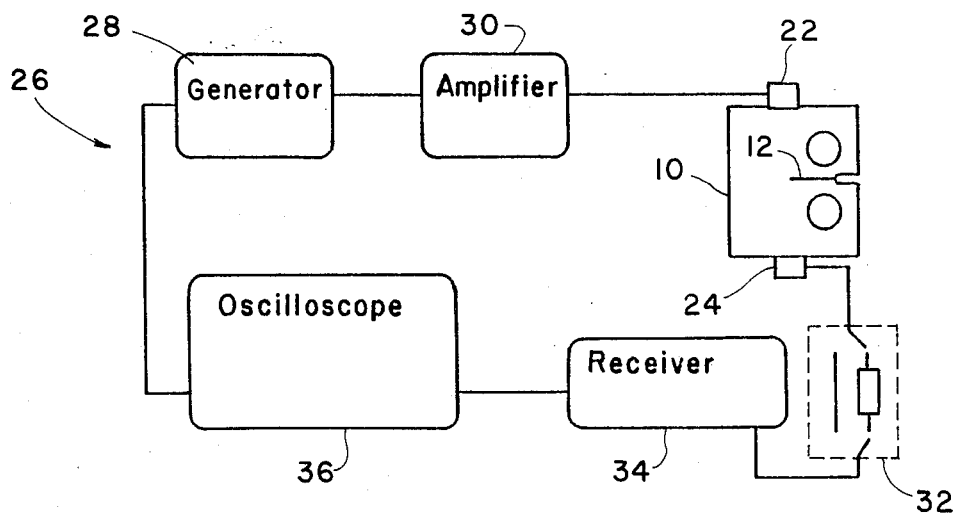

ULTRASONIC METHOD AND APPARATUS FOR DETERMINING CRACK OPENING LOAD

ORIGIN OF THE INVENTION

The invention described herein was made by an employee of the United States Government and may be manufactured and used by or for the government for governmental purposes without payment of any royalties thereon or therefore.

BACKGROUND OF THE INVENTION

1. Field of the Invention

The present invention relates generally to the testing of materials, and more specifically, to an ultrasonic method and apparatus for determining a crack opening load.

2. Description of the Related Art

It is known to test compact tension specimens placed under a load to determine the condition of full crack opening. Referring to FIG. 1, a compact tension specimen 10 has a crack 12 and a notch opening 14 formed at the outer end portion of the crack 12. An extensiometer 16 is placed at the notch opening 14 in order to measure displacement of the notch, and hence, the crack opening. A tension load is applied to the specimen 10 by pulling clevis grips 18 and 20 in opposite directions as indicated by the directional arrows.

Using the apparatus schematically illustrated in FIG. 1, known techniques have been employed for determining crack opening load. The first technique is illustrated in FIGS. 2 and 3 and is known as the "load-reduced displacement" method. In this method, the extensiometer 16 placed at the notch opening 14 measures displacement. By plotting the load on the Y-axis against displacement on the X-axis, determination of reduced displacement leads to a determination of the load at which the crack is actually open. In FIG. 2, "reduced" displacement is determined by the difference between a straight line extrapolation of the upper (straight) data and the measured or actual (curved) data. The extrapolated portion is shown as a broken line and the reduced displacement is indicated by the distance between the broken line and the curved portion of the measured data. The load at which crack opening occurs is illustrated in FIG. 3 as the point at which the reduced displacement does not change with increasing load. As indicated in FIG. 3, this occurs at the vertical portion of the curve.

The second technique is illustrated in FIGS. 4 and 5 and is known as the "load-slope change" method of determining crack opening load. In FIG. 4, load is plotted against displacement as in the load-reduced displacement technique. Changes in slope are measured from regions S1 to S6. Slope increase is plotted in FIG. 5 based on the measured slope changes from FIG. 4. Crack opening is indicated in FIG. 5 where the slope increase changes from perpendicular.

A problem associated with the above-described techniques results from the fact that extensiometers and other similar strain sensors are electrically noisy, and thus, the signals generated by the extensiometers lack the required degree of certainty for precise determination of crack opening load. Another problem is that it is difficult to decide at what point the plot becomes tangent to a line or crosses an axis. The problem is illustrated in FIG. 6 where load is plotted against slope increase. As is evident from FIG. 6, the plotted points of slope increase move to both sides of zero, thereby making determination of an exact crack opening load difficult.

It is generally known to employ acoustic signals to determine the presence of a crack in an object. For example, U.S. Pat. No. 3,911,734 to Mehdizadeh discloses a method of detecting incipient fatigue damage in metal using acoustic emission characteristics obtained during application of a load.

U.S. Pat. No. 4,265,120 to Morris et al. discloses a method of detecting fatigue using acoustic harmonics. A surface acoustic wave is generated at a first position on the object and a harmonic of a generated wave is detected at a second position on the object. The testing method involves relating the characteristics of the detected wave to the remaining useful life of the object.

U.S. Pat. No. 4,522,064 to McMillan discloses an ultrasonic method and apparatus for determining the depth of cracks in pipe or other conduit.

U.S. Pat. No. 4,534,219 to Nadeau et al. discloses a device which relates the frequency of an acoustic wave to an indication of a crack within a test piece.

SUMMARY OF THE INVENTION

An object of the invention is to provide an apparatus for determining precisely when a crack in a compact tension specimen begins to open.

Another object of the invention is to provide a method and apparatus for determining crack opening load without generating signal-interfering noise.

Another object of the invention is to provide an apparatus for determining crack opening load which is relatively simple to operate, inexpensive, and highly accurate.

In a preferred embodiment of the invention, an ultrasonic monitor for determining crack opening load in a specimen having a crack includes an ultrasonic generator outputting a series of tone bursts, a transmit transducer for placement on the specimen and receiving the output of the ultrasonic generator, a receive transducer for placement on the specimen opposite the transmit transducer and receiving acoustic signals passing through a portion of the specimen which includes the crack, and outputting a fundamental output signal and a harmonic output signal, means for converting the transmit transducer output signals into electrical signals, and means for measuring a harmonic amplitude of the converted harmonic signal as an increasing tension load is applied to the specimen to determine a peak harmonic amplitude which indicates crack opening load.

By measuring peak harmonic amplitude, a crack opening load is identified when displacement occurs on the atomic level, meaning that when the crack moves about one Angstrom, this displacement will be identified. Therefore, the present invention provides a highly precise measurement and determination of crack opening load.

In another embodiment of the invention, the receiving transducer is placed on the same side of the test specimen as the transmit transducer, whereby a wave transmitted by the transmitting transducer reflects or bounces off the crack and is received by the receive transducer after interacting with the crack as a second harmonic signal. The receive transducer may be positioned in proximity to the transmit transducer, or it may be stacked on top of the transmit transducer.

These objects, together with other objects and advantages which will be subsequently apparent reside in the details of construction and operation of the ultrasonic monitor for determining crack opening load as more fully hereinafter described and claimed, reference being had to the accompanying drawings forming a part hereof, wherein like reference numerals refer to like parts throughout.

BRIEF DESCRIPTION OF THE DRAWINGS

FIG. 7 is a schematic view of a compact test specimen and a portion of the ultrasonic monitor for determining crack opening load according to the present invention;

FIG. 8 is a schematic, block diagram illustrating an ultrasonic monitor for determining crack opening load according to the present invention; and FIG. 9 is a graph plotting harmonic amplitude against tension load, as measured by the ultrasonic monitor of FIG. 8.

DESCRIPTION OF THE PREFERRED EMBODIMENTS

Figure 1:
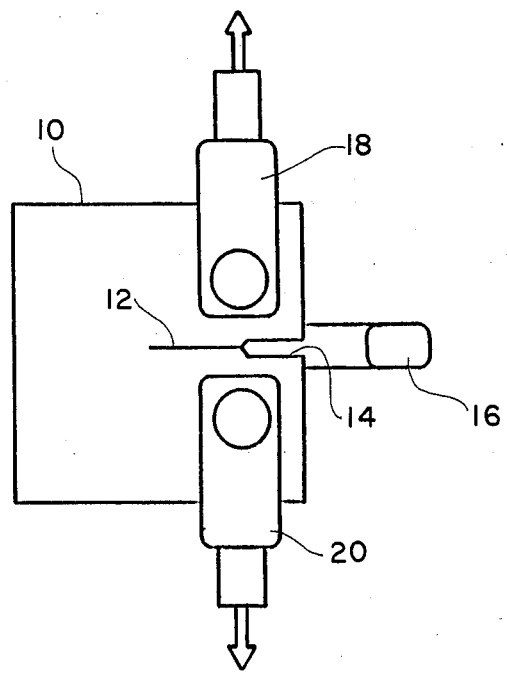
FIG. 1 is a schematic view of a known apparatus for determining crack opening load.
Figure 2:
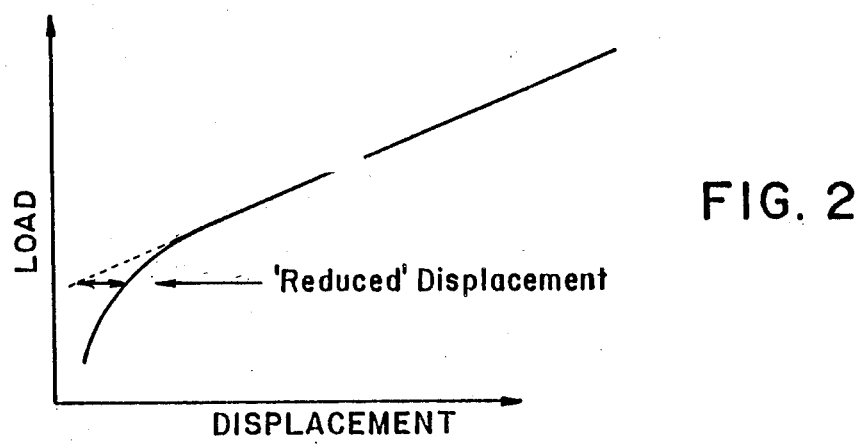
FIG. 2 is a graph plotting load against displacement and illustrating reduced displacement according to a known method of determining crack opening load.
Figure 3:
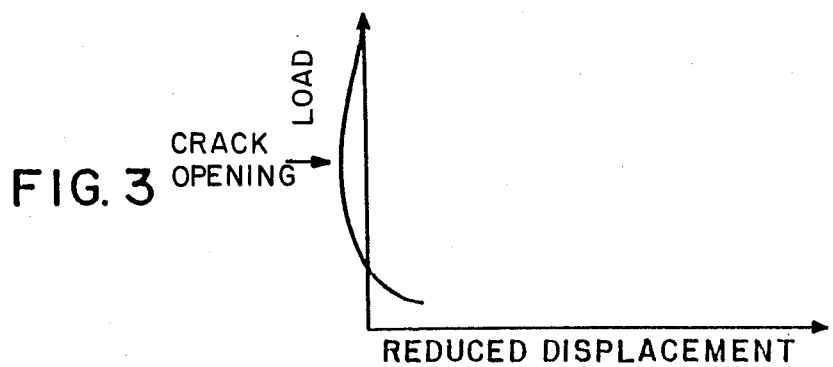
FIG. 3 is a graph plotting load against reduced displacement and illustrating the level of crack opening load of the FIG. 2 method.
Figure 4:
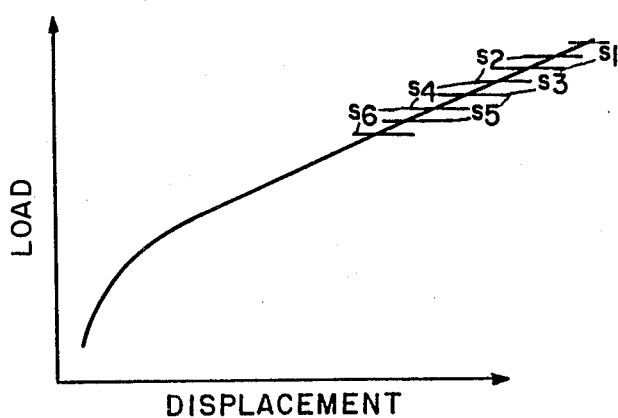
FIG. 4 is a graph plotting load against displacement, illustrating areas of measurement for determining change of slope according to another known method of determining crack opening load.
Figure 5:
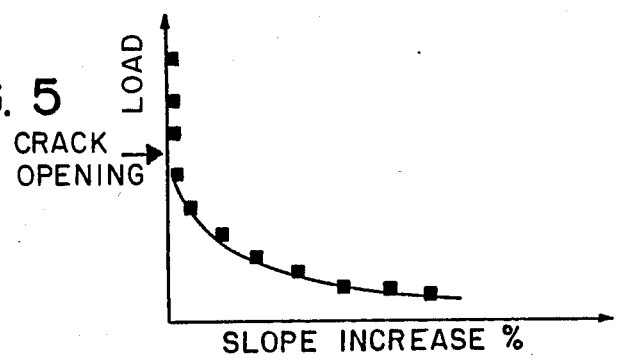
FIG. 5 is a graph plotting load against slope increase and illustrating the crack opening load level of the FIG. 4 method.
Figure 6:
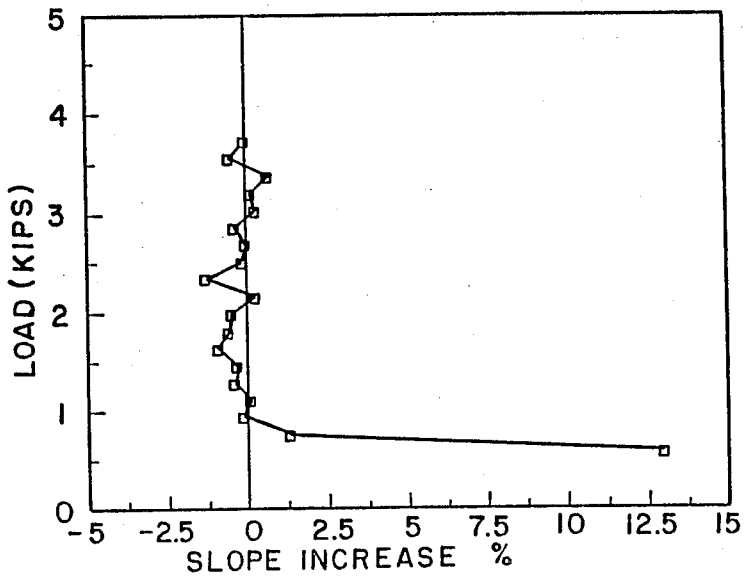
FIG. 6 is a graph showing load plotted against slope increase based on an actual test of crack opening load for a compact tension specimen according to the FIG. 4 method.

Referring now to FIG. 7, a compact test specimen 10 has a crack 12 and a notch opening 14. Test specimens to be tested are generally standardized in terms of length and thickness. Clevis grips 18 and 20 apply a tension force to the compact tension specimen 10 by moving in opposite directions as indicated by the directional arrows. A transmit transducer 22 receives and transmits an ultrasonic signal into the test specimen 10. A receive transducer 24 is located on an opposite side of the compact tension specimen 10 from the transmit transducer 22. Acoustic signals passing between transducer 22 and 24 pass through the cracked region of crack 12.

An ultrasonic system 26 of the present invention is illustrated in FIG. 8. A signal generator 28 outputs a series of tone bursts of a specific frequency, such as 5 MHz, and is connected to an amplifier 30 where the tone bursts are amplified. The transmit transducer 22 is connected to the amplifier 30 for receiving the amplified tone bursts. The transducer 22 is connected to the specimen 10 and excites an acoustic tone burst in the compact tension specimen 10 in the form of a wave which propagates towards the cracked region of crack 12. When the crack is closed, the acoustic wave is transmitted across the cracked region by the portions of the two surfaces that are in intimate contact. The crack alters the 5 MHz signal (f) to generate a second harmonic of the 5 MHz signal due to dislocations in the crystalline structure of the specimen. Thus, a 5 MHz (f) signal and a 10 MHz (2f) signal are simultaneously received by the receive transducer 24, which is connected to the specimen opposite transducer 22. The generation of the second harmonic signal (2f) results from the fact that as the surface of the crack just begins to separate, the wave will only transmit during a portion of the cycle, giving rise to a mechanical "rectification" of the acoustic signal. The effect of a barely opened crack is to enrich the relative portion of the 2f signal.

The acoustic tone burst, as altered by the crack 12, is received by a 10 MHz transducer 24. The output is received by the transducer 24 at both the f and 2f frequencies. Both frequencies pass through a circuit 32 which allows selective switching of the f and 2f signals to a receiver 34. The 10 MHz 2f signal is switched to receiver 34 where it is amplified. The 5 MHZ f signal is switched through an attenuator 33 before passing to the receiver 34 which is connected to the circuit 32. The receiver 34 is first manually tuned to the f signal, and then after switching, is retuned to the 2f signal. The output of the receiver 34 is monitored by an oscilloscope 36, which is connected to the receiver and synchronized with generator 28.

While holding the received fundamental output fixed (5 MHz) an increasing load is applied to the compact tension specimen 10 through clevis grips 18 and 20.

Retuning of the receiver 34 at different loads generates a measurable harmonic output (10 MHz) which is plotted as a function of load in FIG. 9.

As seen in FIG. 9, harmonic amplitude increases at an increasing rate until the curve peaks, the peak indicating the point of crack opening; thereafter, harmonic amplitude falls sharply.

Referring again to FIG. 7, another embodiment of the invention involves placing the transmit and receive transducers on the same side of the compact tension specimen 10. A receive transducer 23 is shown in broken lines on the same side as transmit transducer 22. The transmit and receive transducers are arranged such that a wave transmitted by the transmit transducer reflects or bounces off the crack 12 and is received by the receive transducer 23. The wave transmitted by transmit transducer 22 interacts with the crack to produce the same second harmonic as which is produced by the wave passing through the cracked region.

Frequencies other than those mentioned above can be used. Also, other frequencies generated by the acoustic rectification described above could be monitored. The harmonically generated ultrasonic signal generated by acoustic rectification determines when the crack is fully open. By using an ultrasonic signal, a favorable signal to noise ratio is achieved while maintaining substantial noise immunity from the operation of the load frame and its associated parts.

The many features and advantages of the present invention are apparent from the detailed specification, and thus, it is intended by the appended claims to cover all such features and advantages of the ultrasonic monitor which fall within the true spirit and scope of the invention. Further, since numerous modifications and changes will readily occur to those skilled in the art based upon the disclosure herein, it is not desired to limit the invention to the exact construction and operation illustrated and described. Accordingly, all suitable modifications and equivalents may be resorted to falling within the scope and the spirit of the invention.

What is claimed is:

1. An ultrasonic apparatus for determining crack opening load in a specimen having a crack and under a variable tension load, comprising:
   an ultrasonic generator for outputting a series of tone bursts;
   a transmit transducer for placement on the specimen and receiving the output of the ultrasonic generator;
   a receive transducer for placement on the specimen, and receiving acoustic signals which have interacted with the crack, and outputting a fundamental output signal and a harmonic output signal;
   conversion means for converting the output signals of the receive transducer into electrical signals; and
   means for measuring a harmonic amplitude of the converted harmonic output signals as said variable tension load applied to the specimen increases to determine a peak harmonic amplitude which indicates crack opening load.

2. An ultrasonic apparatus according to claim 1, wherein the receive transducer is placed on the specimen on a side opposite the transmit transducer and receives acoustic signals passing through a portion of the specimen which includes the crack.

3. An ultrasonic apparatus according to claim 1, wherein the receive transducer is placed on the same side of the specimen as the transmit transducer and receives acoustic signals reflecting off the crack.

4. An ultrasonic apparatus according to claim 1, further comprising an amplifier for amplifying the output of the ultrasonic generator.

5. An ultrasonic apparatus according to claim 1, wherein the measuring means comprises an oscilloscope.

6. An ultrasonic apparatus according to claim 1, wherein the ultrasonic generator outputs a 5 MHz tone burst, the transmit transducer is a 5 MHz transducer and the receive transducer is a 10 MHz transducer.

7. An ultrasonic apparatus according to claim 1, wherein the transmit transducer excites an acoustic tone burst in the specimen as an acoustic wave which is mechanically rectified by the crack to generate a second harmonic of the acoustic tone burst.

8. An ultrasonic apparatus according to claim 7, wherein the conversion means comprises a receiver coupled to the oscilloscope and to the receive transducer.

9. An ultrasonic apparatus according to claim 8, further comprising a circuit disposed between the receiver and the receive transducer and including an attenuator and switch for switching to the attenuator, the attenuator attenuating the received fundamental output of the receive transducer, a harmonic output of the receive transducer being switched directly to the receiver.

10. An ultrasonic method for determining crack opening load in a specimen having a crack, comprising the steps of:
    sending an ultrasonic wave through a cracked region of the specimen, the crack generating a second harmonic of the ultrasonic wave;
    converting the second harmonic of the ultrasonic wave into an electrical signal; and
    measuring a harmonic amplitude of the converted electrical signal while applying an increasing tension load to the specimen until a peak harmonic amplitude is reached, whereby the peak indicates crack opening load.

11. An ultrasonic method according to claim 10, wherein the step of sending an ultrasonic wave comprises sending a series of tone bursts from an ultrasonic generator to a transmit transducer placed on one side of the specimen, and receiving the ultrasonic wave and a second harmonic of the ultrasonic wave with a receive transducer placed on an opposite side of the specimen, the cracked region being disposed between the transmit transducer and the receive transducer.

12. An ultrasonic method for determining crack opening load in a specimen having a crack, comprising the steps of:
    sending an ultrasonic wave into a cracked region of the specimen, the wave interacting with the crack to generate a second harmonic of the wave which is reflected from the cracked region;
    receiving the reflected second harmonic of the ultrasonic wave;
    converting the reflected second harmonic of the ultrasonic wave into an electrical signal; and
    measuring a harmonic amplitude of the reflected, converted electrical signal while applying an increasing tension load to the specimen until a peak harmonic amplitude is reached, whereby the peak indicates crack opening load.

* * * * *